United States Patent [19]

Beck

[11] Patent Number: 5,034,226

[45] Date of Patent: Jul. 23, 1991

[54] COSMETIC PRODUCT

[76] Inventor: Julius H. Beck, Winkelstrasse 4, Horw, Switzerland

[21] Appl. No.: 157,748

[22] Filed: Feb. 19, 1988

[30] Foreign Application Priority Data

Feb. 20, 1987 [CH] Switzerland ............................ 648/87

[51] Int. Cl.$^5$ ...................... A61K 35/78; A61K 7/06; A61K 35/12; A61K 35/28

[52] U.S. Cl. .................................... 424/195.1; 424/74; 424/520; 424/579; 514/557; 514/844; 514/845; 514/846; 514/847; 514/848

[58] Field of Search ............... 514/844, 845, 846, 847, 514/848, 557; 424/195.1, 74, 95, 43, 44, 520, 579

[56] References Cited

U.S. PATENT DOCUMENTS

| | | | |
|---|---|---|---|
| 130,720 | 8/1872 | Johnson | 424/74 |
| 136,308 | 2/1873 | Curtis | 424/195.1 X |
| 367,406 | 8/1887 | Jones | 424/195.1 X |
| 939,431 | 11/1909 | Muller | 424/74 |
| 3,947,568 | 3/1976 | Bates et al. | 424/47 |
| 4,702,913 | 10/1987 | Marty | 424/95 |
| 4,784,847 | 11/1988 | Zullinger-Bopp et al. | 424/195.1 X |

FOREIGN PATENT DOCUMENTS

| | | | |
|---|---|---|---|
| 1390184 | 6/1963 | France | 424/95 |
| 4209M | 7/1966 | France | 424/95 |
| 8101514 | 6/1981 | France | 424/95 |
| 19899 | of 1895 | United Kingdom | 424/74 |
| 6904 | of 1913 | United Kingdom | 424/74 |

Primary Examiner—John W. Rollins
Attorney, Agent, or Firm—William J. Barber

[57] ABSTRACT

A content of a sparkling wine, particularly champagne prepared in champagne-like manner unexpectedly increases the effectiveness of cosmetic products. Preferably most of the aqueous phase of such products comprises liquid constituents of such sparkling wine, particularly champagne.

33 Claims, No Drawings

COSMETIC PRODUCT

BACKGROUND OF THE INVENTION

The invention relates to a cosmetic product having an aqueous phase.

The aqueous phase contained in such cosmetic products, serving as a carrier for many different substances, conventionally consists of water. Every effort is made when producing such products to ensure that nothing can lead to problems in the product or during its subsequent use. It is therefore an established rule to only use ultrapure water, i.e. water demineralized by distillation or in some other way.

Swiss patent 563 162 (1975) describes a cosmetic product mainly prepared on the basis of ethyl alcohol. EP-AS 196 340 (1986) describes a cosmetic product based on a mixture of ethanol and grape wine. Federal Republic of Germany patent P 36 05 570 (1986) describes a product for tightening human skin parts based on rum. Finally, Swiss patent application 659 943 (1987) which was filed on Mar. 13, 1987 describes an antiseptic product based on wine and honey.

SUMMARY OF THE INVENTION

The problem of the present invention is to provide cosmetic products with improved characteristics compared with the known forms.

Comprehensive tests performed with this objective have surprisingly revealed that products with an unexpectedly increased activity are obtained if they contain a sparkling wine produced in champagne-like manner and in particular champagne.

Therefore the problem of the invention is solved by providing cosmetic products containing at least liquid and solid constituents of a sparkling wine prepared in a champagne-like manner in free or bonded form.

Particularly satisfactory results are obtained if the aqueous phase, normally consisting of demineralized water, is at least largely formed by liquid constituents of a sparkling wine, particularly champagne. Sparkling wine of the aforementioned type and in particular champagne obtained from the Pinot-Noir vine type give particularly surprising activities in cosmetic products. White sparkling wine of the aforementioned type, particularly champagne is not only relatively neutral in color, but has a favorable effect on its characteristics, a Blanc-de-Noir, particularly if produced from Pinot-Noir grapes, being eminently suitable for the purposes of the invention.

However, white sparkling wine of the aforementioned type and preferably champagne, even when produced from white grapes is very suitable in many cases. Rosé sparkling wine or champagne can be successfully used where its coloring action is not considered to be disadvantageous; this applying to an increased extent with respect to red sparkling wine or champagne.

Initially clarity does not exist regarding the reason for such surprising effects. Although to some extent speculative, it is considered that the reason for the surprising effects of sparkling wine of the aforementioned type and particularly champagne in the inventive cosmetic products can be clarified. However, the information given below is provided under the express reservation that the invention as such is not influenced by any incorrect speculations contained therein.

Analysis of champagne carried out by the inventor revealed, apart from water, the following constituents.

Mineral substances: compounds of Ca, K, Na, Mg, Mn, Fe, B, Si, Cl, I and Cu (in all approximately 3% by weight).

Nitrogen compounds: albumins, proteins, xanthine, sarcine, choline, proline, p-lysine, histidine, arginine, crystine and lecithin.

Carbohydrates: dextrose, pentose, starch sugars, levulose and glucose.

Natural acids: tartaric, maleic, lactic, silicic, benzoic, citric, salicylic and volatile acids (in all approximately 5 to 9% by weight).

Vitamins: A, B1, B2, B5, B6, C and D.

Alcohols: ethyl alcohol, butylene glycol, sorbitol and mannitol.

Natural dyes: oenin, xanthophyll and carotene.

Champagne contains a number of skin-friendly constituents in balanced combination. In retrospect, it is surprising that champagne has not previously been used as a carrier of the substances contained therein and others of a cosmetic product and that the "empty" demineralized water has not at least partly been replaced by this donor of skin-friendly substances in the aqueous phase.

The aforementioned naturally formed, skin-friendly characteristics of champagne can be ideally combined with the latest renutritive repair complexes (containing cell extract) and give effects like those aimed at by modern cosmetics Cell formation and renewal is accelerated. The capacity of the skin to store moisture is increased and at the same time more moisture is supplied. The biological equilibrium of the skin is favorably influenced. As a result of the bacteriological action skin-harmful germs are eliminated, but the healthy skin flora is retained. Irritated skin is calmed and made more resistant.

Thus, the activation of cell formation slows down the ageing process, so that skin stays young and fresh for a longer period of time. As a result of the improse moisture conditions, tired cells are filled, so that that skin remains elastic and youthful. The supply of biologically valuable substances assists the natural functions of the skin, which also acts against harmful environmental influences and increases the resistance effect, so that the skin can remain healthy and healthy skin is more attractive. From the bacteriological standpoint it is particularly important that the champagne assists the maintenance of the natural acid protection of the skin and acts against the growth of germs, fungi, bacteria, etc and it is also possible to have a favorable influence on acne. Therefore the skin is fine and smooth. Even irritated or sensitive skin can be rapidly claimed by treatment with an inventive product. Inflammation is reduced, microcracks in dry skin are avoided or heal rapidly and pore-deep cleaning can be obtained, accompanied by disinfection.

All this encourages the maintaining and formation of soft, velvety, youthful healthy skin, which is the aim of all cosmetics.

An inventive cosmetic product can be very easily absorbed in the skin. A prickly freshness which can be attributed to the champagne can be looked upon as especially pleasant. An inventive cosmetic product can e.g. be in the form of cleaning milk, face lotion, day cream, night cream, eye liner, face mask, day and night repair, peeling cream, body lotion and the like.

Three examples of inventive cosmetic products are now described, together with the production thereof (pbw standing for parts by weight).

EXAMPLE 1

The following are melted and mixed at 75° C.:
12.00 pbw polyglycerol oleate (Hostacerin by Hoechst)
2.00 pbw of cetyl stearyl alcohol (Emulgade by Henkel)
3.00 pbw of paraffin oil
4.00 pbw of neutral oil (Miglyol)
3.00 PCL-liquid (Dragoco)
0.03 pbw of butyl hydroxyanisole (Oxynex)
In 60.00 pbw of champagne are dissolved
0.20 pwb of emulsifier (Euxyl K-100 of Schulke & Mayer GmbH, D-2000 Glashutte)
4.00 pbw of propylene glycol
2.00 pbw of cattle spleen extract (Revitalin-P of Pentapharm Ltd., Basle, Switzerland)
3.00 pbw of carbohydrate (Pentavitin of Pentapharm Ltd., Basle, Switzerland) and after heating to 75° C.
0.50 pbw of acrylic acid polymer (Carbopol by Goodrich) are allowed to swell and
0.70 pbw of trimethanol amine are added dissolved in
4.00 pbw of water Accompanied by constant stirring the champagne-containing liquid is added to the aforementioned melt, cooled to approximately 55° C., homogenized and cooled to approximately 30° C., after which
0.10 pbw of Kathon CG (a preservative) and
0.40 pbw of perfume are added and stirred cold.

The leads to an excellent day cream with the aforementioned characteristics.

EXAMPLE 2

The following are heated to 75° C., melted and mixed
3.0 pbw of sorbitan sesquioleate
5.0 pbw of petrol lanolin alcohol (Amerchol CAB by Americhol, USA)
2.5 pbw of isopropyl myristate
0.5 pbw of Dragonsantol (by Dragoco)
20.0 pbw of paraffin wax (Lunacera PEP by Fuller, Germany)
0.5 pbw of preservative ((Oxynex 2004 by Merck, AG, Darmstadt, Germany)
In 53.95 pbw of champagne are dissolved and heated to 75° C.
0.1 pbw of preservative (Kanthon CG by Christ, Basle, Switzerland)
0.2 pbw of hydroxymethyl-dioxo-imidazolinyl (Germall 115, by Sutton Labs.)
0.3 pwb of MgSO4-H2O
4.0 pbw of cattle spleen extract (Revitalin-P by Pentapharm Ltd., (Basle, Switzerland)
5.0 pbw of eye connective tissue (cell extract—Pentaglycan by Pentapharm Ltd., Basle, Switzerland)
5.0 pbw of Sorbitol 60 (Karion F by Merck AG Darmstadt, Germany)

Accompanying by constant stirring, the hot champagne-containing liquid is added to the first-mentioned hot melt, cooled to approximately 30° C. and then 0.4 pbw of perfume are added, thoroughly mixed and cooled to room temperature.

An eye liner with an unexpectedly high activity is obtained.

EXAMPLE B 3

Heating takes place to 70° C., followed by melting and mixing of
6.0 pbw of sorbitan sesquioleate (Arlacel 83 by Atlas/ICI)
2.0 pbw of polyethylene-sorbitan trioleate (Tween 85 by Atlas/ICI)
5.0 pbw of 2-octyl-dodecanol
5.0 pbw paraffin oil
4.0 pbw of beeswax
4.0 pbw of isopropyl palmitate
4.0 pbw of neutral oil (Miglyol of Dynamit Nobel, Germany)
1.0 pbw of aluminum stearate
2.0 pbw of lanolin
0.5 pbw of preservative (Phenonip of Nipa Labs., Great Britain)
In 54.3 pbw of champagne are dissolved and heated to 70° C.
4.0 pbw of propylene glycol
2.0 pbw of glycerol
0.1 pbw of allantoin
0.3 pbw of magnesium sulphate
0.3 pbw of hydroxymethyl-dioxo-imidazolinyl (Germall 115 of Sutton Labs., USA)
5.0 pbw of cattle spleen extract (Revitalin-P by Pentapharm Ltd., Basle, Switzerland).

Accompanied by constant stirring, the hot, champagne-containing liquid is added to the first-mentioned hot melt and cooled to 35° C. 0.5 pbw of perfume is then added thereto, whisked and cooled to room temperature. This gives a night cream having an above-average activity.

I claim:

1. A cosmetic product with an aqueous phase comprising constituents of a sparkling wine prepared in accordance with a champagne-making method and added to the cosmetic product.

2. A cosmetic product according to claim 1 wherein the constituents of said sparkling wine are liquid and form a major part of the aqueous phase.

3. A cosmetic product according to claim 2 wherein said constituents of said sparkling wine are derived from champagne prepared from Pinot-Noir grapes.

4. A cosmetic product according to claim 2 wherein said constituents of said sparkling wine are derived from champagne.

5. A cosmetic product according to claim 2 wherein said liquid constituents are derived from a Rosé sparkling wine.

6. A cosmetic product according to claim 1 wherein said constituents of said sparkling wine are derived from champagne prepared from Pinot-Noir grapes.

7. A cosmetic product according to claim 6 wherein said constituents of said sparkling wine are derived from sparkling white wine.

8. A cosmetic product according to claim 1 wherein said constituents of said sparkling wine are derived from champagne.

9. A cosmetic product according to claim 8, wherein said constituents comprise mineral substances including Ca, K, Na, Mg, Mn, Fe, B, Si, Cl, I and Cu, nitrogen compounds including albumins, proteins, xanthine, sarcine, choline, pyroline, p-lysine, histidine, arginine, crystine and lecithin, carbohydrates including dextrose, pentose, starch sugars, levulose and glucose, natural acids including tartaric, maleic, lactic, silicic, benzoic, citric, salicylic and volatile acids, vitamins including A, B1, B2, B5, B6, C and D, alcohols including ethyl alcohol, butylene glycol, sorbitol and mannitol, and natural dyes including oenin, xanthophyll and carotene.

10. A cosmetic product according to claim 9, wherein the total amount of said natural acids in said product is approximately 5 to 9% by weight.

11. A cosmetic product according to claim 1 wherein said constituents are derived from a Rosé sparkling wine.

12. A cosmetic product including an aqueous phase comprising a champagne-containing liquid.

13. A cosmetic product according to claim 12, wherein said champagne-containing liquid is prepared from Pinot-Noir grapes.

14. A cosmetic product according to claim 12, further including a cell extract selected from the group consisting of an eye connective tissue and cattle spleen extract.

15. A cosmetic product comprising an aqueous phase comprising a champagne-containing liquid and a cell extract selected from the group consisting of an eye connective tissue and cattle spleen extract.

16. A night cream comprising a champagne-based liquid having a champagne substantially prepared from Pinot-Noir grapes, said champagne being dissolved and heated in combination with at least the following: propylene glycol, glycerol, allantoin, magnesium sulphate, hydroxymethyl-dioxo-imidazolinyl, cattle spleen extract.

17. A night cream as claimed in claim 16, wherein the champagne-based liquid has about 54.3 parts by weight of the champagne, which is dissolved and heated to a predetermined temperature with all of the following:
    (i) 4.0 parts by weight of propylene glycol,
    (ii) 2.0 parts by weight of glycerol,
    (iii) 0.1 parts by weight of allantoin,
    (iv) 0.3 parts by weight of magnesium sulphate,
    (v) 0.3 parts by weight of hydroxymethyl-dioxo-imidazolinyl, and
    (vi) 5.0 parts by weight of cattle spleen extract.

18. A night cream as claimed in claim 17, wherein the champagne-based liquid is further dissolved at the predetermined temperature with sorbitan sesquioleate, polyethylene-sorbitan trioleate, 2-octyl-dodecanol, paraffin oil, beeswax, isopropyl palmitate, neutral oil, aluminum stearate, lanolin, and a preservative.

19. A night cream as claimed in claim 16, wherein the champagne is substantially prepared from Blanc-de-Noir grapes.

20. A method for making a night cream comprising the step of:
    (a) making a first liquid by mixing and melting at a first predetermined temperature the following
        (i) 6.0 parts by weight of sorbitan sesquioleate,
        (ii) 2.0 parts by weight of polyethylene-sorbitan,
        (iii) 5.0 parts by weight ob 2-octyl-dodecanol,
        (iv) 5.,0 parts by weight of paraffin oil,
        (v) 4.0 parts by weight of beeswax,
        (vi) 4.0 parts by weight of isopropyl palmitate,
        (vii) 4.0 parts by weight of neutral oil,
        (viii) 1.0 parts by weight of aluminum stearate,
        (ix) 2.0 parts by weight of lanolin, and
        (x) 0.5 parts by weight a preservative;
    (b) making a champagne-based liquid by dissolving and heating to the predetermined temperature 54.3 parts by weight of champagne with the following
        (i) 4.0 parts by weight of propylene glycol,
        (ii) 2.0 parts by weight of glycerol,
        (iii) 0.1 parts by weight of allantoin,
        (iv) 0.3 parts by weight of magnesium sulphate,
        (v) 0.3 parts by weight of hydroxymethyl-dioxo-imidazolinyl, and
        (vi) 5.0 parts by weight of cattle spleen extract;
    (c) making a night cream liquid by adding the first liquid together with the champagne-based liquid while constantly stirring;
    (d) cooling the night cream liquid to a second predetermined temperature in which in becomes a night cream.

21. A method for making a night cream as claimed in claim 20, including the further step of adding 0.5 parts by weight of a perfume.

22. An eyeliner comprising a champagne substantially prepared from Pinot-Noir grapes, which is dissolved together with at least the following: hydroxymethyl-dioxo-imidazolinyl, MgSO$_4$-H$_2$O, cattle spleen extract, eye connective tissue, Sorbitol 60.

23. An eyeliner cream as claimed in claim 22, wherein said eyeliner cream consists of 53.9 parts by weight of champagne which is first dissolved and heated with the following:
    (i) 0.2 parts by weight hydroxymethyl-dioxo-imidazolinyl,
    (ii) 0.3 parts by weight MgSO$_4$H$_2$O,
    (iii) 4.0 parts by weight cattle spleen extract,
    (iv) 5.0 parts by weight eye connective tissue, and
    (v) parts by weight Sorbitol 60.

24. A eyeliner as claimed in claim 23, wherein the champagne is further dissolved with the following: sorbitan sesquioleate, petrol lanolin alcohol, isopropyl myristata, Dragonsantol, paraffin wax, and preservative.

25. An eye liner as claimed in claim 22, wherein the champagne is substantially prepared from Blanc-de-Noir grapes.

26. A method for making eye liner comprising the step of:
    (a) making a first liquid by mixing and melting at a first predetermined temperature the following
        (i) 3.0 parts by weight of sorbitan sesquioleate,
        (ii) 5.0 parts by weight of petrol lanolin alcohol,
        (iii) 2.5 parts by weight of isopropyl myristata,
        (iv) 0.5 parts by weight of Dragonsantol,
        (v) 20.0 parts by weight of paraffin wax,
        (vi) 0.5 parts by weight of preservative,
    (b) making a champagne-based liquid by dissolving and heating 53.95 parts by weight of champagne with the following
        (i) 0.2 parts by weight hydroxymethyl-dioxo-imidazolinyl,
        (ii) 0.3 parts by weight MgSO$_4$-H$_2$O,
        (iii) 4.0 parts by weight cattle spleen extract,
        (iv) 5.0 parts by weight eye connective tissue,
        (v) 5.0 parts by weight Sorbitol 60;
    (c) making an eye liner liquid by adding the first liquid together with the champagne-based liquid while constantly stirring; and
    (d) cooling the eye liner liquid to a second predetermined temperature and into an eye liner.

27. A method for making an eye liner as claimed in claim 26, including the further step of adding 0.4 parts by weight of a perfume.

28. A day cream comprising a champagne-based liquid substantially prepared from Pinot-Noir grapes, which is dissolved together with at least the following: emulsifier, propylene glycol, cattle spleen extract, carbohydrate, acrylic acid polymer, trimethanol amine, and water.

29. A day cream as claimed in claim 28, wherein the champagne-based liquid is further dissolved with the following: acrylic acid polymer, trimethanol amine and water.

30. A day cream as claimed in claim 28, wherein said day cream consists of 60.0 parts by weight of champagne which is first dissolved and heated with the following:
   (i) 0.20 parts by weight of emulsifier,
   (ii) 4.0 parts by weight of propylene glycol,
   (iii) 2.0 parts by weight of cattle spleen extract,
   (iv) 3.0 parts by weight of carbohydrate;
   after heating the second liquid to the predetermined temperature, adding 0.5 parts by weight of acrylic acid polymer and allowing it to swell;
   dissolving into the second liquid 0.7 parts by weight of trimethanol amine already dissolved in 4.0 parts by weight of water.

31. A day cream as claimed in claim 28, wherein the champagne is substantially prepared from Blanc-de-Noir grapes.

32. A method for making a day cream comprising the steps of:
   (a) making a first liquid by mixing and melting at a first predetermined temperature the following
      (i) 12.0 parts by weight of polyglycerol oleate,
      (ii) 2.0 parts by weight of cetyl stearyl alcohol,
      (iii) 3.0 parts by weight of paraffin oil,
      (iv) 4.0 parts by weight of neutral oil,
      (v) 3.0 parts by weight of PCL-liquid,
      (vi) 0.03 parts by weight butyl hydroxyanisole;
   (b) making a champagne-based liquid by heating 60.0 parts by weight of champagne and dissolving into it the following
      (i) 0.20 parts by weight of emulsifier,
      (ii) 4.0 parts by weight of propylene glycol,
      (iii) 2.0 parts by weight of cattle spleen extract,
      (iv) 3.0 parts by weight of carbohydrate;
   (c) after further heating the champagne-based liquid to the predetermined temperature, adding 0.5 parts by weight of acrylic acid polymer and allowing it to swell;
   (d) dissolving into the champagne-based liquid 0.7 parts by weight of trimethanol amine already dissolved in 4.0 parts by weight of water;
   (e) making a day cream liquid by adding the first liquid together with the champagne-based liquid while constantly stirring; and
   (f) cooling the day cream liquid to a second predetermined temperature and into a day cream.

33. A method for making a day cream as claimed in claim 32, including the further step of adding 0.4 parts by weight of a perfume and 0.10 parts by weight of Kathon CG.

* * * * *